US00PP28716P3

(12) United States Plant Patent
Pierce

(10) Patent No.: US PP28,716 P3
(45) Date of Patent: Nov. 28, 2017

(54) ***CALIBRACHOA* PLANT NAMED 'CBRZ0008'**

(50) Latin Name: *Calibrachoa hybrida*
Varietal Denomination: CBRZ0008

(71) Applicant: SYNGENTA PARTICIPATIONS AG, Basel (CH)

(72) Inventor: Robert O. Pierce, Watsonville, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,832

(22) Filed: Oct. 20, 2015

(65) Prior Publication Data

US 2016/0286707 P1 Sep. 29, 2016

(30) Foreign Application Priority Data

Mar. 26, 2015 (CA) ..... PBR 15/8545

(51) Int. Cl.
*A01H 5/02* (2006.01)

(52) U.S. Cl.
USPC ..... Plt./413

(58) Field of Classification Search
USPC ..... Plt./413
See application file for complete search history.

(56) References Cited

PUBLICATIONS

UPOV PLUTO—plant varity database—International Union for the Protection of New Plant Varieties citation for 'CBRZ0008', Jan. 12, 2017 (1 page total).*

* cited by examiner

*Primary Examiner* — Susan McCormick Ewoldt
(74) *Attorney, Agent, or Firm* — Dale Skalla

(57) ABSTRACT

A new *Calibrachoa* plant named 'CBRZ0008' particularly distinguished by the mid-sized purple flowers with a darker "eye" and yellow inside the flower at the base of the petals, green foliage, good branching, late flowering, and a moderately compact, semi-trailing plant habit, and has little sensitivity to soil pH.

1 Drawing Sheet

Latin name of the genus and species of the plant claimed: *Calibrachoa hybrida.*

Varietal denomination: 'CBRZ0008'.

BACKGROUND OF THE NEW PLANT

The present invention comprises a new *Calibrachoa*, botanically known as *Calibrachoa hybrida*, and hereinafter referred to by the variety name 'CBRZ0008'.

'CBRZ0008' is a product of a planned breeding program. The new cultivar has mid-sized purple blue flowers with a darker "eye" and yellow inside the flower at the base of the petals, green foliage, good branching, late flowering, and a moderately compact, semi-trailing plant habit, and has little sensitivity to soil pH.

'CBRZ0008' originated from a hybridization made in December 2010 in a greenhouse in Gilroy, Calif., USA. The female parent was the commercial plant variety 'Mini Famous Compact Plum'. CBRZ0008 has blue flowers and is more trailing and 'Mini Famous Compact Plum' is more compact with plum flowers. The male parent of 'CBRZ0008' was an unpatented proprietary plant characterized as a blue flowered plant, known as 1861-1, originating from a seedling selected in Gilroy, Calif.

The resulting seeds were sown in March 2011 and 'CBRZ0008' was selected as one flowering plant within the progeny of the stated cross in June 2011 in a controlled environment in Gilroy, Calif.

The first act of asexual reproduction of 'CBRZ0008' was accomplished when vegetative cuttings were propagated from the initial selection in the fall of 2011 in a controlled environment in Gilroy, Calif.

BRIEF SUMMARY OF INVENTION

Horticultural examination of plants grown from cuttings of the plant initiated in the spring of 2012, and continuing thereafter, has demonstrated that the combination of characteristics as herein disclosed for 'CBRZ0008' are firmly fixed and are retained through successive generations of asexual reproduction.

'CBRZ0008' has not been observed under all possible environmental conditions. The phenotype may vary significantly with variations in environment such as temperature, light intensity, and day length.

A Plant Breeder's Right for this cultivar was applied for in Canada on Mar. 26, 2015, No. 15/8545.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'CBRZ0008' with colors being as true as possible with an illustration of this type.

Figure 1:
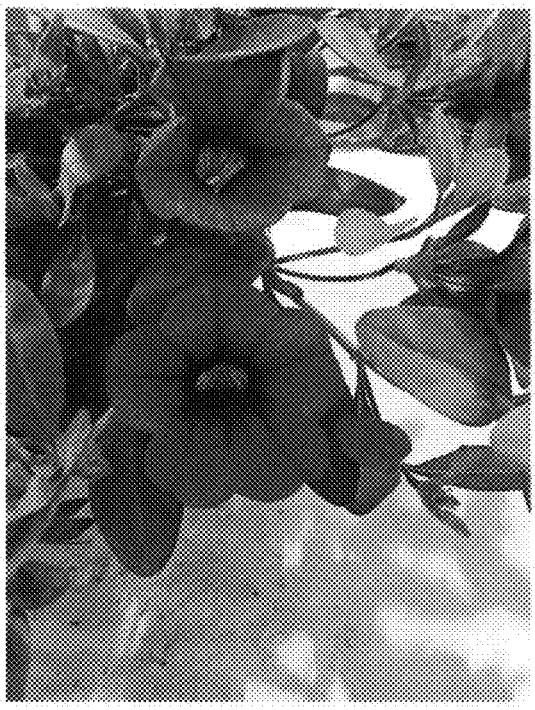
Figure 2:
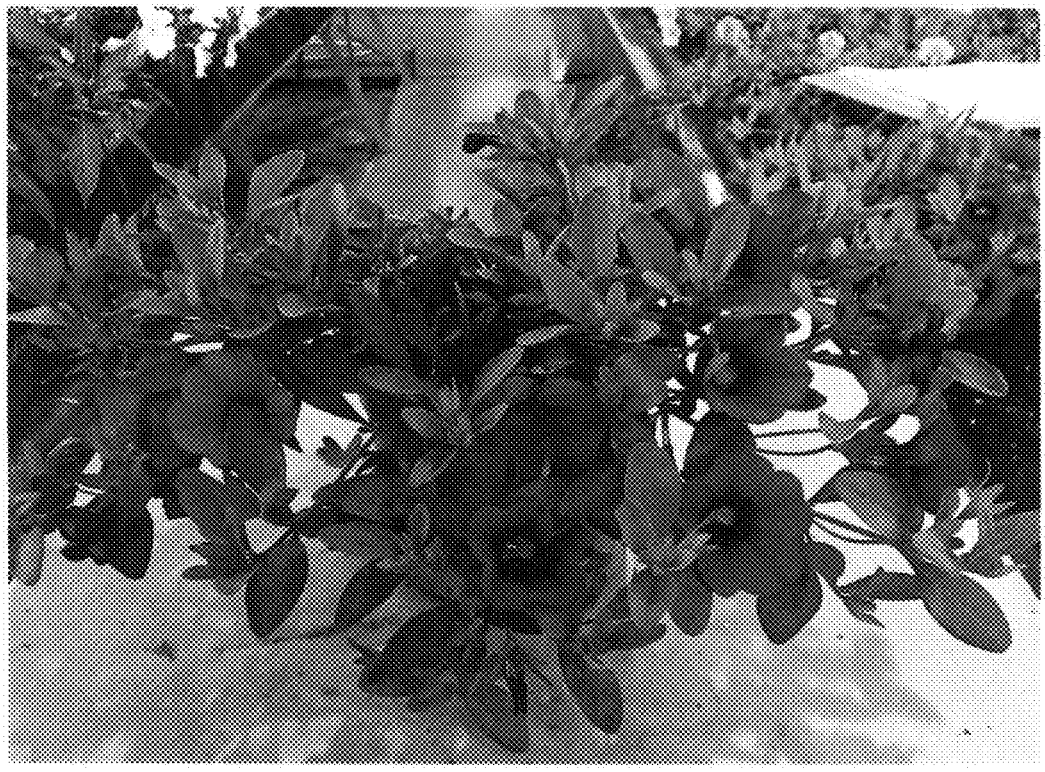

The photographic drawing shows in FIG. 1. a close-up of the flowers and in FIG. 2. a flowering plant of the new variety.

DETAILED BOTANICAL DESCRIPTION

The aforementioned photographs were taken outdoors on Apr. 20, 2015 in Andijk, The Netherlands.

The measurements and observations were made on in Gilroy, Calif. on plants grown both in an outdoor and indoor trial.

Color references are made to The Royal Horticultural Society Colour Chart (R.H.S.) 2001.

TABLE 1

DIFFERENCES BETWEEN THE NEW VARIETY 'CBRZ0008' AND A SIMILAR VARIETY

| | 'CBRZ0008' | 'Mini Famous Blue' (unpatented) |
|---|---|---|
| Main flower color: | Bluish color with less tendency to fading | Stronger fading on the outer edge |
| Color of throat: | Deeper yellow | Lighter yellow |
| Plant habit as a young plant: | More round | More trailing |

Plant:

*Form, growth and habit*.—Semi-upright stems, compact and mounding, very well branched.

*Plant height*.—4.5-5.0 inches.

*Plant height* (*inflorescence included*).—About 5.0 inches.

*Plant width*.—35 inches.

*Quantity of main branches*.—16-20.

*Quantity of secondary branches*.—4-6 per basal branch.

*Time to produce a flowering plant*.—7-8 weeks for a 12 cm pot (from planting of rooted cuttings).

Roots:

*Number of days to initiate*.—18-21 days at about 22° C.

*Number of days to produce a rooted cutting*.—21-24 days at 22° C.

*Type*.—Fibrous.

*Color*.—RHS 158D.

Stem:

*Color of stem*.—Mainly RHS 145A.

*Length of stem*.—Approximately 7-11 cm.

*Diameter*.—0.15-0.2 cm.

*Length of internodes*.—1.7-2.0 cm.

*Texture*.—Smooth, hairless.

Foliage:

*Immature leaf, color of upper surface*.—RHS 146A.

*Immature leaf, color of lower surface*.—RHS 146C.

*Mature leaf, color of upper surface*.—RHS 146A.

*Mature leaf, color of lower surface*.—RHS 146B.

*Leaf blade, length*.—2.0-2.3 cm.

*Leaf, width*.—0.5-0.7 cm.

*Shape*.—Elliptical, narrow.

*Base shape*.—Acuminate.

*Apex shape*.—Obtuse.

*Margin*.—Entire.

*Texture*.—Hairless.

*Color of veins, upper surface*.—RHS 146A.

*Color of veins lower surface*.—RHS 146C.

*Petiole color*.—RHS 146B.

*Petiole length*.—0.1-0.3 cm.

*Diameter of petiole*.—0.1 cm.

*Texture*.—Smooth.

Inflorescence:

*Type*.—Flowers solitary in upper leaf axis and slanting upright or outwards.

*Quantity of inflorescences per plant*.—Approximately 15-20.

*Lastingness of individual flowers*.—About 7-9 days.

*Fragrance*.—None.

*Duration of flowering*.—Continuous flowering throughout the summer.

Pedicel:

*Color of pedicel*.—RHS 146D.

*Length of pedicel*.—3-5 mm.

*Diameter of pedicel*.—1.0 mm.

*Texture of pedicel*.—Smooth, hairless.

Flower:

*Immature flowers, corolla upper surface*.—RHS 83A.

*Immature flowers, corolla lower surface*.—RHS 153C.

*Mature flowers, color upper surface*.—RHS 81A with a somewhat deeper, purple ring, RHS 83A in the center around the throat opening. Deep in throat is a yellow color RHS 154B.

*Mature flowers, color lower surface*.—RHS 81A.

*Flower horizontal diameter*.—2.5-3.1 cm.

*Flower height* (*vertical*).—0.9-1.0 cm.

*Corolla tube length*.—About 1.1 cm.

*Petal apex shape*.—Truncate.

*Margin*.—Entire.

*Waviness of petals*.—Weak to medium.

*Petal lobation*.—Moderate.

*Corolla texture*.—'Face' papillose and glabrous; rear side with short hair.

*Corolla tube color inside*.—RHS 154B.

*Corolla tube color outside*.—RHS N81B.

Bud (just before opening):

*Color at apex*.—RHS 83A.

*Length*.—2.8-3.0 cm.

*Width* (*upper end*).—0.5-0.6 cm.

*Shape*.—Oblong.

Calyx:

*Number of sepals*.—5.

*Color of sepals, adaxial or upper surface*.—RHS 138A.

*Color of sepals, abaxial or lower surface*.—RHS 138A.

*Length of sepals*.—10-12 mm.

*Width of sepals*.—5-7 mm.

*Sepal shape*.—Lanceolate.

*Apex shape*.—Obtuse to acute.

*Margins*.—Entire.

*Texture*.—Smooth.

Reproductive organs:

*Pistil*.—1.

*Length*.—1.3 cm.

*Style color*.—RHS 145B.

*Style length*.—0.8-0.9 cm.

*Stigma color*.—RHS 144B.

*Number of stamens*.—5.

*Color of filaments*.—RHS 4D.

*Length filaments*.—0.7-1.1 cm.

*Color of pollen*.—RHS 13B.

*Pollen amount*.—Moderate.

*Fertility/seed set*.—Not observed on this hybrid.

*Disease/pest resistance*.—Not observed on this hybrid.

What is claimed is:

1. A new and distinct variety of *Calibrachoa* plant named 'CBRZ0008', substantially as illustrated and described herein.

* * * * *